United States Patent
Granger et al.

(10) Patent No.: US 8,139,671 B2
(45) Date of Patent: Mar. 20, 2012

(54) CONTACTLESS TRANSMISSION OF ELECTRICAL SIGNALS BETWEEN TWO UNITS

(75) Inventors: Robin Granger, Winchester (GB); Helmut Repp, Erlangen (DE); Michael James Sisson, Hants (GB)

(73) Assignee: Siemens Aktiengesellschaft, Munich (DE)

( * ) Notice: Subject to any disclaimer, the term of this patent is extended or adjusted under 35 U.S.C. 154(b) by 874 days.

(21) Appl. No.: 12/113,472

(22) Filed: May 1, 2008

(65) Prior Publication Data

US 2008/0279302 A1 Nov. 13, 2008

(30) Foreign Application Priority Data

May 8, 2007 (DE) .......................... 10 2007 021 597

(51) Int. Cl.
*H04B 15/00* (2006.01)
(52) U.S. Cl. ...................................................... 375/285
(58) Field of Classification Search .................. 375/285, 375/130, 295, 296, 316; 439/17; 307/11, 307/147
See application file for complete search history.

(56) References Cited

U.S. PATENT DOCUMENTS

| 4,223,313 A | 9/1980 | Chabrol |
| 5,140,696 A | 8/1992 | Fox |
| 2006/0089009 A1* | 4/2006 | Krumme ........................ 439/13 |

FOREIGN PATENT DOCUMENTS

| DE | 28 45 438 | 4/1979 |
| DE | 197 26 949 A1 | 1/1998 |
| DE | 102 19 959 A1 | 11/2003 |
| DE | 103 19 248 A1 | 12/2004 |

OTHER PUBLICATIONS

German Office Action dated Nov. 7, 2007 with English translation.

* cited by examiner

*Primary Examiner* — Khai Tran
(74) *Attorney, Agent, or Firm* — Lempia Summerfield Katz LLC

(57) ABSTRACT

The invention discloses an arrangement and an associated method for contactless transmission of electrical signals between two units 1, 2, wherein a first unit 1 has a transmitting element 11 emitting electrical signals and at least one conductor 13 connected thereto, and wherein a second unit 2 has a receiving element 29 and a coupling element 31 connected thereto. The coupling element 31 is formed by means of a resistance material and decouples an electrical signal carried in the conductor 13.

14 Claims, 1 Drawing Sheet

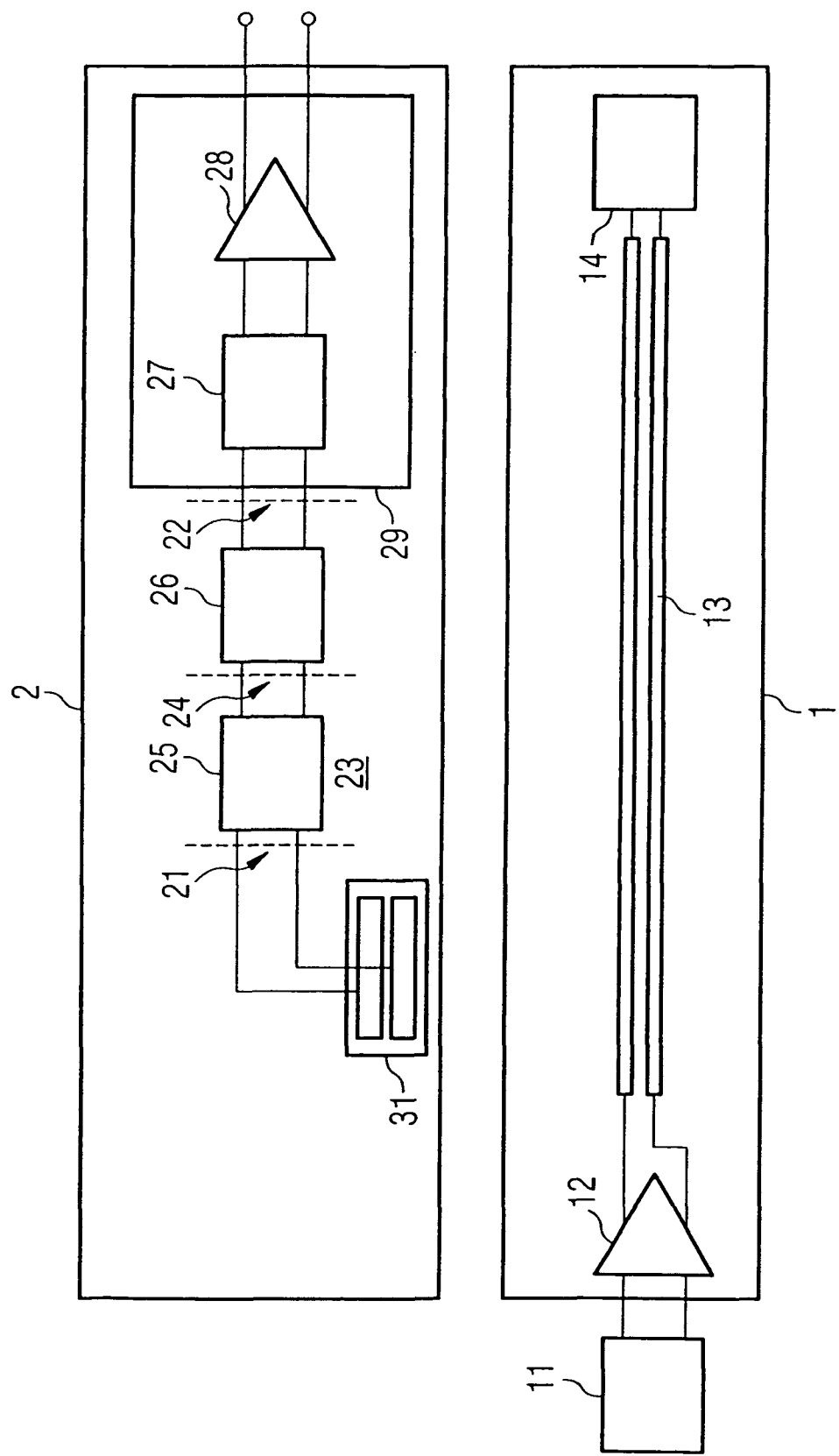

CONTACTLESS TRANSMISSION OF ELECTRICAL SIGNALS BETWEEN TWO UNITS

This patent document claims the benefit of DE 10 2007 021597.7, filed May 8, 2007, which is hereby incorporated by reference.

BACKGROUND

The present embodiments relate to contactless transmission of electrical signals between two units.

Electrical signals are transmitted between units that are moving relative to one another. In the case of a computed tomography system, for example, the data captured by rotating x-ray detectors is forwarded to a stationary part of the computed tomography system. The stationary part may process the data, slideways and slipcollector rings are used for the transmission. The electrical signal that is supplied to a conductor is diverted by a movable tap. Taps may include contact springs or carbon rods that establish a galvanic contact, alternatively, DE 2845438 describes electrical signals that are transmitted contactlessly using a capacitive or inductive coupling.

A broadband signal transmission between units that are moving relative to one another includes sophisticated high-frequency transmission technology. During transmission, the effect of interference radiation or sensitivity to irradiation should be minimized. In addition, the signal transmission should be low in terms of noise and distortion.

A data source of, for example, a moving unit delivers a discrete symbol sequence including a sequence of binary symbols (e.g., −1 and +1) or a sequence of multilayer symbols (e.g. −7, −5, −3, −1, +1, +3, +5 and +7). The absolute value of the range of the discrete symbol sequence is negligibly low below a limit frequency, so a perfect reconstruction of the symbol sequence in a receiver is also possible even if a weakening distortion of the signal components occurs below the limit frequency during a transmission between the data source and a receiver. Symbol sequences may be generated, for example, using the 8B/10B or 64B/66B encoding used in a plurality of data transmission standards or another method for generating such symbol sequences.

The discrete symbol sequence is converted into an analog signal using a line driver. The analog signal is injected into a line. The signal is terminated at the end with its characteristic wave impedance. The symbols are converted into an analog signal at a fixed data rate. Mathematically, this process can be described as the convolution of an equidistant Dirac pulse sequence whose pulse strengths correspond to the values of the symbol sequence with an analog transmit pulse. The shape of the analog transmit pulse depends on the frequency response of the line driver. A nonlinear pre-distortion, which may be referred to as pre-emphasis, of the analog data signal may be performed in the line driver. The nonlinear pre-distortion results in an unmodulated data signal in the baseband. The spectrum of the analog data signal may have zeros on the line in the case of integer multiples of the symbol rate. In the range below the limit frequency the spectrum is negligibly small.

The line may be, for example, a single line on which the data signal is transmitted in basic mode, or a parallel-routed dual line on which the data signal is transmitted in differential mode.

A stray signal of the line in the local area is contacttessly tapped with a metallic structure, which may be referred to as a coupling element. The metallic structure does not touch the line but is immediately adjacent to the line and can be moved along the line. The shape of the line may be irrelevant. For example, the line may be shaped as a straight line guide for data transmission to translatorily movable units or a circular line guide for data transmission to rotating units.

The weak electrical signal tapped by the coupling element is routed via a line to an amplifying receiving element. Linear, passive filtering may be performed before routing the electrical signal. Linear amplifiers or nonlinear amplifiers, such as limiting amplifiers or comparators, may be used, for example, as the amplifying input stage of the receiving element. The transmitted symbol sequence is then reconstructed with a circuit for reconstructing the symbol timing of the transmission and a sampling of the received data signal.

During the transmission of the electrical signal, decoupling a stray field, if the data rate is greater than approximately ten times the lower limit frequency, may be problematic. Decoupling the stray field leads to interfering reflections at the limits of the coupling element and to interfering propagation delay effects within the coupling element. As a result, the data transmission is prone to errors. Interferences may be avoided if the geometric dimensions of the coupling element are considerably smaller than the smallest wavelength that is to be transmitted.

The signal quality of the digital data transmission may be assessed with an eye diagram from digital data transmission technology. The data stream is subdivided into sections of equal length which are a multiple of the symbol duration in length. The sections are written on top of one another with a persistent oscilloscope or memory oscilloscope. An image in the form of an eye is produced on the screen. If the dimensions of the coupling element are great, a closed eye or a small eye opening is formed in the associated eye diagram, due to reflections. A closed eye or a small eye opening is a sign of a poor digital signal transmission.

For low-frequency signal components, however, reflections and delay effects at the coupling element due to its dimensions are irrelevant. The coupling may be modeled approximately as a discrete capacitance between line and coupling element. If the distance of the coupling element from the line cannot be reduced due to ancillary mechanical conditions, for example, tolerances or insulation gap, this capacitive coupling remains weak. With a low lower limit frequency, the input impedance of the amplifier circuit of the receiving element is highly resistive in order to be able to transmit the low-frequency signal components nonetheless. Otherwise the opening of the eye in the eye diagram is reduced, such that data transmission does not occur.

Characteristic wave impedance matching of the line to the receiver, which is required for a low-reflection transmission, cannot be implemented technically, since high-resistance lines, for example, cannot be produced on printed circuit boards. Accordingly, undesirable reflections result on the line between coupling element and receiving element. At high data rates, the reflections distort the data signal, which prevents an error-free reconstruction of the data in the receiving element.

A small capacitive coupling may not adequately drive parasitic elements of the circuit components that are present at the input of the amplifier circuit of the receiving element. The maximally transmissible bit rate may be limited. Stability problems at the amplifier may occur if the chosen input impedance is too high.

The input impedance of the amplifier circuit of the receiving element may be highly resistive, as a result of which the maximally transmissible bit rate is disadvantageously limited.

SUMMARY AND DESCRIPTION

The present embodiments may obviate one or more of the drawbacks or limitations inherent in the related art. For example, in one embodiment, a transmission system provides a contactless low-noise and low-distortion signal transmission between two units at a high bit rate.

In one embodiment, a system, for contactless transmission of electrical signals includes a first unit and a second unit. The electrical signals are transmitted between the first unit and the second unit. The first unit includes a transmitting element, which emits electrical signals, and at least one conductor connected to the transmitting element. The second unit includes a receiving element and a coupling element connected to the receiving element. An electrical signal, which is carried in the conductor, may be decoupled by the coupling element. The coupling element is a resistance material or a metal and a resistance material The metal and the resistance material overlap in at least one area.

The electrical resistance of a resistance material may be between 1 and 500 ohm per square. "Ohm per square" indicates the specific resistance normalized to the layer thickness.

The resistance material may include, for example, resistive ink, resistive screen printing paste, or resistive film.

The resistance material may cause the reflected signal components in the coupling element, which have a longer propagation delay to the output of the coupling element, to be more strongly attenuated than those signal components, which reach the output of the coupling element without reflections and with a shorter propagation delay.

In one embodiment, the eye opening is maximized as a result of the different attenuation in the coupling element and the noise sensitivity of the signal transmission may be optimized.

In one embodiment, the dimensions of the coupling element and the coupling capacitance of the coupling element may be increased without degrading the quality of the signal transmission.

Since a resistive material is used for the coupling element, a fine-tuning of the resistivity of the coupling element is not required, despite manufacturing tolerances, since the value of the resistivity has no influence over a wide range.

The first unit and the second unit may be moved relative to each other.

The first unit may have two parallel conductors that transmit the electrical signals in differential mode.

The coupling element may be connected to at least one connecting line of the second unit via a resistance network of the second unit matching the characteristic wave impedance.

The input impedance of the input amplifier circuit of the receiving element may be scaled down, which may reduce the maladjustment to supplying lines.

In one embodiment, a computed tomography system may include a system for contactless transmission of electrical signals.

BRIEF DESCRIPTION OF THE DRAWINGS

FIG. 1 illustrates one embodiment of signal transmission with a coupling element.

DETAILED DESCRIPTION

FIG. 1 shows a transmission system including a first unit 1, second unit 2, and transmitting element 11. An analog differential electrical signal is transmitted from the transmitting element 11 into the first unit 1. In the first unit 1, the signal is transmitted along a dual line 13 via a line driver 12 to the terminating resistance 14. Parts of the signal, which is carried in the dual line 13, are contactlessly decoupled by a coupling element 31 in a second unit 2. In the second unit 2, the parts of the signal are supplied to the input of a receiving element 29 of the second unit 2 via a resistance network 25 and connecting lines 26. The receiving element 29 comprises an impedance matching circuit with filtering entity 27 and an amplifier 28. From the receiving element 29, the signal is supplied to a signal processing entity.

Due to reflections in the coupling element 31, the overcoupled analog signal components may reach the output of the coupling element 31 over different electromagnetic propagation paths. The propagation paths may cause the signal components to have different propagation delays. The signal components of the propagation paths, which may overlay one another, form an output signal of the coupling element 31. If the length dimension of the coupling element 31 is too great, the differences in propagation delay of the differently delayed signal components become so great compared to the bit rate that intersymbol interferences result. Accordingly, the eye may close both horizontally and vertically in the associated eye diagram.

Signal components reflected in the coupling element 31 run longer in the resistance material than unreflected signal components and are therefore more strongly attenuated. A stronger attenuation of the signal components with longer propagation paths results in a lessening of the intersymbol interferences. The eye opening may be enlarged.

The coupling element 31 may include a resistance material, also referred to as resistive material, or a combination of metal and resistance material. The metal and the resistance material may overlap in at least one area. The first and second unit 1,2 may rotate relative to each other. For rotational movements, the resistance material may be symmetrical with respect to the metallic central area. For translatory movements, the resistance material may be asymmetric with respect to the metal.

The conductivity of the resistive material of the coupling element 31 may be chosen, for example, to maximize the eye opening. Accordingly, the noise sensitivity of a data transmission may be optimized.

The coupling element 31 may include resistive material. Propagation delays of the signal propagation paths, which exceed the duration of several bits, may be tolerated because the coupling element 31 includes resistive material. The length of the coupling element 31 is not limited to a fraction of the length of one bit on the line.

For the low-frequency signal components, in which the propagation delay effects at the coupling element 31 are irrelevant, the coupling element 31 is in a quasi-stationary state for each instant in time, since no differences in potential occur at the coupling element 31. Accordingly, no significant compensating currents, which are attenuated by the resistive material, flow in the coupling element 31. For low-frequency signal components, the coupling may correspond to a discrete capacitance. If the distance between line 13 and coupling element 31 remains constant, the discrete capacitance increases proportionally to the surface area spanned between line and coupling element 31. The length of the coupling element 31 may be increased. The surface area spanned between line 13 and coupling element 31 may be increased. The coupling capacitance may be increased.

In one embodiment, the 3 dB limit frequency, which results from the mathematical product of the coupling capacitance, and an input impedance 21 of the circuit 25, 26, 27 connected to the coupling element 31 is set as low as possible. Setting the frequency and coupling capacitance as low as possible may cause an interference-insensitive data transmission with a sufficiently large opening of the eye in the eye diagram. The resistive coupling element 31 may increase the coupling capacitance. Accordingly, a lower input impedance 21 may be realized at a predefined limit frequency.

The increased capacitive coupling may cause an increased eye opening compared to a metallic coupling element.

The dimensions of the coupling element 31 are not restricted to a size limited by the bit rate when the resistive material is used. The coupler capacitance associated with each input impedance 21 of the circuit 25, 26 connected to the coupling element 31 may be chosen such that the low-frequency signal components are also transmitted with sufficient quality.

In one embodiment, the input impedance 21 is based on the line impedance 24 of the connecting line 26 of the coupling element 31 with the input stage of the amplifier 28 in the receiving element 29; an impedance 23 implemented in the resistance network 25; and the input impedance 22 of the receiving element 29, which can be set within certain limits by wiring the amplifier 28 with a filtering entity 27.

Cables and/or plug-in connectors may be used for connecting the coupling element 31 to the receiving element 29. The impedance of cables and plug-in connectors is not freely selectable. 50-ohm cables and plug-in connectors are a common, commercially available standard for transmission at high data rates. Cables and plug-in connectors for 60- or 75-ohm connections may be used, but not high-impedance connection systems with more than one 1 kOhm. If the connecting line 26 or a part of the connecting line 26 is implemented on a printed circuit board as, for example, a stripline or micro-stripline, then the range of usefully realizable line impedances is limited at the top end to several hundred ohms.

In one embodiment, the connecting line 26 is terminated in terms of characteristic wave impedance serially at the end of the coupling element 31 and in parallel at the input of the receiving element 29. The impedance 21 that is effective for calculating the required coupler capacitance may be twice as great as the input impedance 22 of the receiving element. A differential signal transmission may have a coupler capacitance that is four times as great as the line impedance 24. In both cases, there are no interfering reflections on the connecting line 26.

In order to manufacture a coupling element 31 from a resistive material, a screen printing method is used to apply the coupler structure, for example, to an insulating carrier material, referred to as the substrate, having suitable dielectric properties. Pastes, which have a conductivity that is dependent on their composition, may be used for applying the coupler structure. After the printing process, the pastes are stabilized in an oven. The desired resistivity of the material may be set in the oven, not only with the composition of the paste used for the screen printing, but also by changing the thickness of the applied paste layer using different screens and application pressures and by changing the geometric dimensions. In series production tolerances less than 20% may be realized. A test strip may be attached at the edge of the carrier material that is used in the production method for the purpose of adjusting the screen printing process. Adjustment of the resistivity of the coupler structure with laser trimming is also possible, but not necessary for this application, since the sensitivity of the opening of the eye in the eye diagram has a wide maximum as a function of the resistivity.

In another embodiment, an ink jet printer may be used to apply a resistive ink.

A computed tomography system may include a system for contactless transmission of electrical signals. The computed tomography system may transfer the data, which is captured by rotating x-ray detectors, to a stationary part of the computed tomography system. Control data may be transmitted in both directions between the rotating and the stationary part of the system. The computed tomography system may include a differential line that runs along a circular path.

As the development of computed tomography technology advances, the data rate to be transmitted increases constantly. At these high data rates the propagation delay and reflection effects occurring in the coupling element 31 are no longer negligible. A system for conactless transmission of electrical signals and an associated method make it possible, because of the larger dimensions of the coupling element 31 and its resistivity, to operate the components of the receiving element 29 up to the limits of their specified bit rate.

The invention claimed is:

1. A system for contactless transmission of electrical signals, the system comprising:
a first unit including a transmitting element that emits electrical signals and at least one conductor connected to the transmitting element,
a second unit including a receiving element and a coupling element connected to the receiving element, the coupling element being operable to decouple an electrical signal carried in the at least one conductor,
wherein the coupling element includes a resistive material, the resistive material being operable to more strongly attenuate a signal component in the coupling element, which has having a longer propagation delay to an output of the coupling element, than a signal component having a shorter propagation delay.

2. The system as claimed in claim 1, wherein the coupling element includes a metal and the resistive material, the metal and the resistive material overlapping in at least one area.

3. The system as claimed in claim 2, wherein the resistive material is symmetrical with respect to the metal.

4. The system as claimed in claim 1, wherein a value of an electrical resistance of the resistive material is in a range from 1 to 500 ohm per square.

5. The system as claimed in claim 1, wherein the resistive material is resistive ink or resistive screen printing paste.

6. The system as claimed in claim 1, wherein the first unit and the second unit are movable relative to each other.

7. The system as claimed in claim 1, wherein the first unit includes two parallel conductors that transmit the electrical signals in a differential mode.

8. The system as claimed in claim 1, wherein the coupling element is connected to at least one connecting line of the second unit via a resistance network of the second unit that matches a characteristic wave impedance.

9. The system as claimed in claim 1, wherein an input of the receiving element has a low impedance.

10. The system as claimed in claim 1, wherein the first unit and second unit are disposed in a computed tomography system.

11. A method for contactless transmission of electrical signals between a first unit and a second unit having a coupling element, the method comprising:
decoupling an electrical signal carried in the first unit using the coupling element including a resistive material; and
attenuating a signal component of the decoupled electrical signal that has a longer propagation delay to an output of the coupling element, more than a signal component of the decoupled electrical signal that has a shorter propagation delay using the resistive material of the coupling element.

12. The method as claimed in claim 11, wherein the coupling element is formed from a metal and from the resistive material, the metal and the resistive material overlapping in at least one area.

13. The method as claimed in claim 12, wherein the resistive material is symmetrical with respect to the metal.

14. The method as claimed in claim 11, wherein a value of an electrical resistance of the resistive material is in a range from 1 to 500 ohm per square.

* * * * *